US00PP30304P2

(12) United States Plant Patent
Kobayashi et al.

(10) Patent No.: US PP30,304 P2
(45) Date of Patent: Mar. 19, 2019

(54) ***ZOYSIA MATRELLA* PLANT NAMED 'FOX'**

(50) Latin Name: *Zoysia matrella*
Varietal Denomination: Fox

(71) Applicants: National Agriculture and Food Research Organization, Tsukuba-shi (JP); Chubu Co., Ltd., Tohaku-gun (JP)

(72) Inventors: Makoto Kobayashi, Nasushiobara (JP); Shigemitsu Kasuga, Nasushiobara (JP); Masumi Ebina, Nasushiobara (JP); Shin-ichi Tsuruta, Nasushiobara (JP); Shigeaki Yamada, Tohaku-gun (JP); Shinnosuke Oota, Tohaku-gun (JP); Yasuyuki Uozumi, Tohaku-gun (JP)

(73) Assignees: National Agriculture and Food Research Organization, Tsukuba-shi (JP); Chubu Co., Ltd., Tohaku-gun (JP)

( * ) Notice: Subject to any disclaimer, the term of this patent is extended or adjusted under 35 U.S.C. 154(b) by 0 days.

(21) Appl. No.: 15/732,035

(22) Filed: Sep. 8, 2017

(51) Int. Cl.
*A01H 5/12* (2018.01)

(52) U.S. Cl.
USPC ..... Plt./390

(58) Field of Classification Search
USPC ..... Plt./390
See application file for complete search history.

*Primary Examiner* — Annette H Para
(74) *Attorney, Agent, or Firm* — Oblon, McClelland, Maier & Neustadt, L.L.P.

(57) ABSTRACT

A new and distinct variety of *Zoysia matrella* plant named 'Fox', characterized by having less ear emergence, dark green leaf color, thick stolon, high tolerance to tread pressure, better summer survival, late fall discoloration, and high disease resistance, as compared to other *Zoysia* grass varieties.

22 Drawing Sheets

Specification includes a Sequence Listing.

Latin name of genus and species of plant claimed: The Latin name of the genus and species of the novel variety disclosed herein is *Zoysia matrella*.

Variety denomination: The novel variety of *Zoysia matrella* disclosed herein has been given the variety denomination 'Fox'.

BACKGROUND OF THE INVENTION

The present invention relates to a new and distinct perennial variety of *Zoysia matrella*, which was obtained in 1994, from the crossbreeding between the ecotype '286 Togurazaki 6' (seed parent, unpatented and unnamed, collected in Minamitane town, Kumage-county, Kagoshima-prefecture, Japan) and the ecotype '226 Nagasaki Akase 6' (pollen parent, unpatented and unnamed, collected in Katsumoto town, Iki-county, Nagasaki-prefecture, Japan) in National Institute of Livestock and Grassland Science, Tochigi-prefecture, Japan. The 10 $F_1$ individuals derived from the above-mentioned crossbreeding were maintained by vegetative propagation, and in 2003 to 2006, the 8th individual was selected by its properties of less ear emergence, dark green leaf color, thick stolon, better summer survival, late fall discoloration, and high disease resistance, and referred to as 'Fox'.

At the same time as the above-mentioned selection, 'Fox' was tested by being compared to 'Emerald' and 'Meyer', both of which are the most morphologically and physiologically similar varieties to 'Fox' (the first comparison tests). In addition, further comparison tests of 'Fox' with 'Emerald' and 'Meyer' were carried out in 2013 to 2015 (the second comparison tests). Furthermore, 'Fox' was tested with regard to tolerance to tread pressure, by being compared to 'El Toro', which is the standard variety of *Zoysia japonica*.

'Fox' is a distinct, vegetatively propagated variety of *Zoysia matrella*. 'Fox' is the varietal denomination of this new *Zoysia* grass. The name 'Fox' may also designate this plant in commerce.

SUMMARY OF THE INVENTION

The invention relates to a new and distinct variety of *Zoysia matrella* plant named 'Fox,' as described and illustrated herein. Specifically, 'Fox' is a new and distinct perennial variety of *Zoysia matrella*, characterized by having less ear emergence, dark green leaf color, thick stolon, high tolerance to tread pressure, better summer survival, late fall discoloration, and high disease resistance.

BRIEF DESCRIPTION OF THE FIGURES

The accompanying colored photographs (FIGS. 1-20) illustrate and compare the overall appearance of the new *Zoysia matrella* plant, showing the colors as true as it is reasonably possible to obtain in colored reproductions of this type. Colors in the photographs may differ slightly from the color values cited in the detailed botanical description which accurately describe the actual colors of the plant.

DETAILED DESRIPTION OF THE VARIETY

The following is a detailed description of the new *Zoysia matrella* grass variety known as 'Fox', based upon observations of the plant grown in pots and close planted fields.

'Fox' is a perennial, vegetatively propagated *Zoysia* grass, and is believed to be a variety of *Zoysia matrella* due to its morphological properties. The seed parent of 'Fox' was the ecotype '286 Togurazaki 6' (unpatented and unnamed), and the pollen parent was the ecotype '226 Nagasaki Akase 6' (unpatented and unnamed). The applicants had vegetatively propagated 'Fox' by sod, and discovered that 'Fox' is a new and distinct variety compared to 'Emerald' and 'Meyer' (both of which are the most morphologically and physiologically similar varieties to 'Fox). 'Fox' is characterized by its less ear emergence, dark green leaf color, thick stolon, high tolerance to tread pressure, better summer survival, late fall discoloration, and high disease resistance, compared to other *Zoysia* grass varieties.

Figure 1:
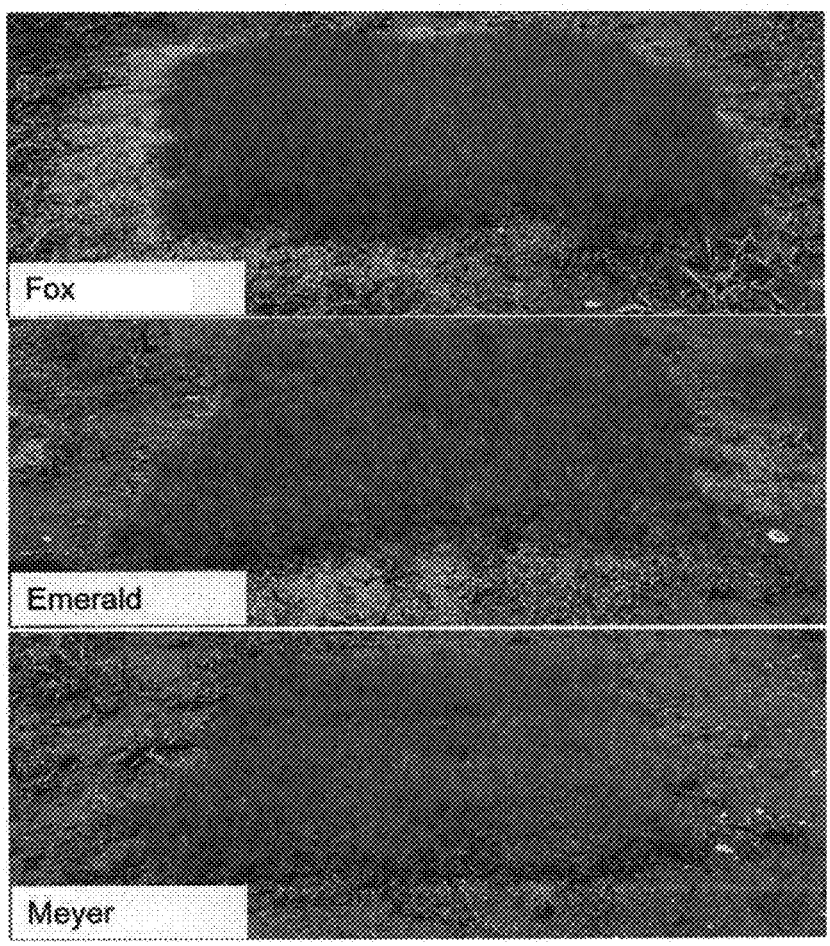
FIG. 1 shows a comparison of leaf colors of 'Fox', 'Emerald,' and 'Meyer'. Photographing date: Jul. 21, 2015. Photographing site: test field in Nasu research center of National Institute of Livestock and Grassland Science, National Agriculture and Food Research Organization: Senbonmatsu, Nasushiobara city, Tochigi prefecture, Japan.
Figure 21:
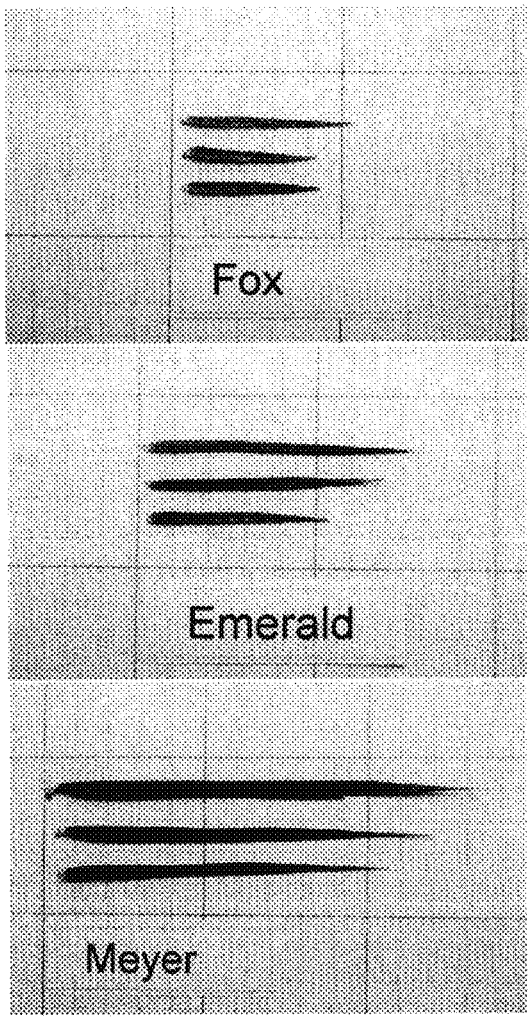
FIG. 21 shows the leaf blade tip shapes of 'Fox' (upper), 'Emerald' (middle) and 'Meyer' (bottom). The dotted lines show 5 mm square, and the bold lines show 25 mm square.
Figure 22:
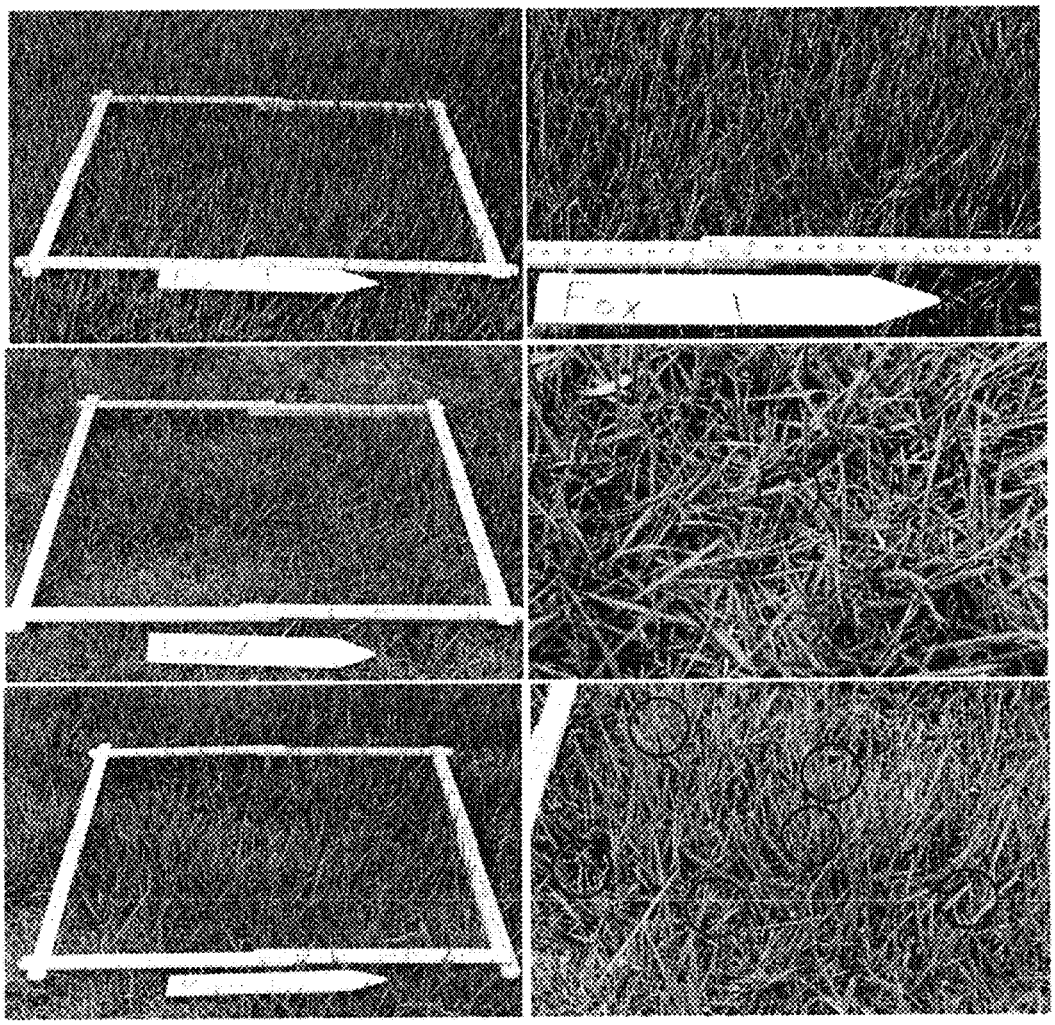
FIG. 22 shows ear emergence of 'Fox' (upper), 'Emerald' (middle) and 'Meyer' (bottom). The photographs in the left columns show the quadrats for counting ear emergence of each variety, and those in the right columns show the close-up of the ear emergence parts in the quadrats. The ear emergence parts of each variety are marked by red circles.

'Fox' has acute leaf blade tip (see FIG. 21), and 'Fox' has less ear emergence than 'Meyer' (see Tables 1 and 2 below, and FIG. 22). In addition, the comparison of leaf colors of 'Fox', 'Emerald' and 'Meyer' (FIG. 1) shows that the leaf color of 'Fox' is darker than 'Emerald'. Since 'Fox' has less ear emergence than 'Meyer', and has darker leaf color than 'Emerald', 'Fox' is more aesthetically appealing as a whole than 'Emerald' and 'Meyer'.

Figure 2:
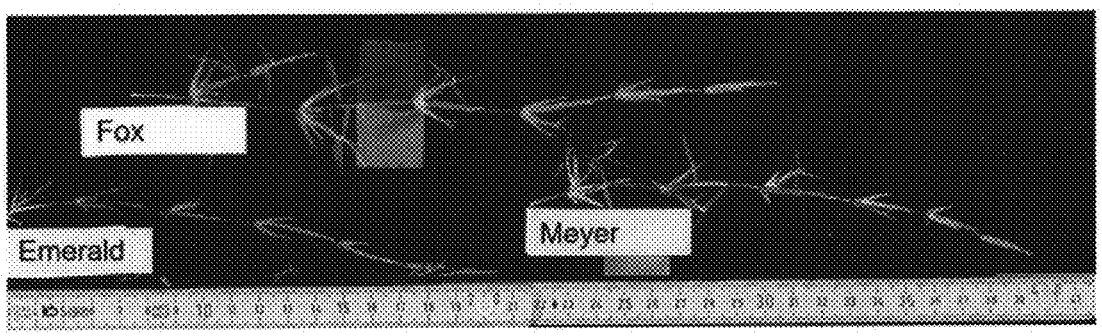
FIG. 2 shows a comparison of stolon thicknesses and stolon lengths (in cm) of 'Fox', 'Emerald' and 'Meyer'.
Figure 3:
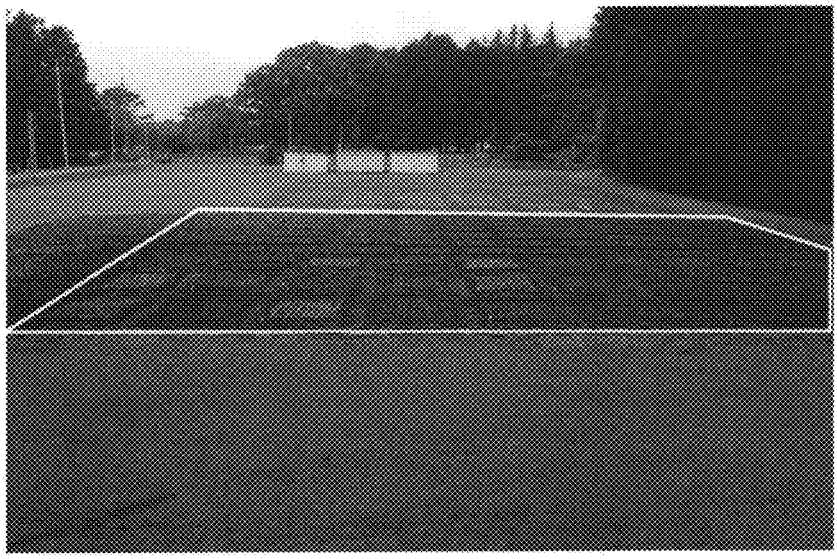
FIG. 3 shows a panoramic view of the test field (in the white frame border), including the test plot of 'Fox'. Photographing date: Jul. 18, 2013. Photographing site: same as in FIG. 1.
Figure 4:
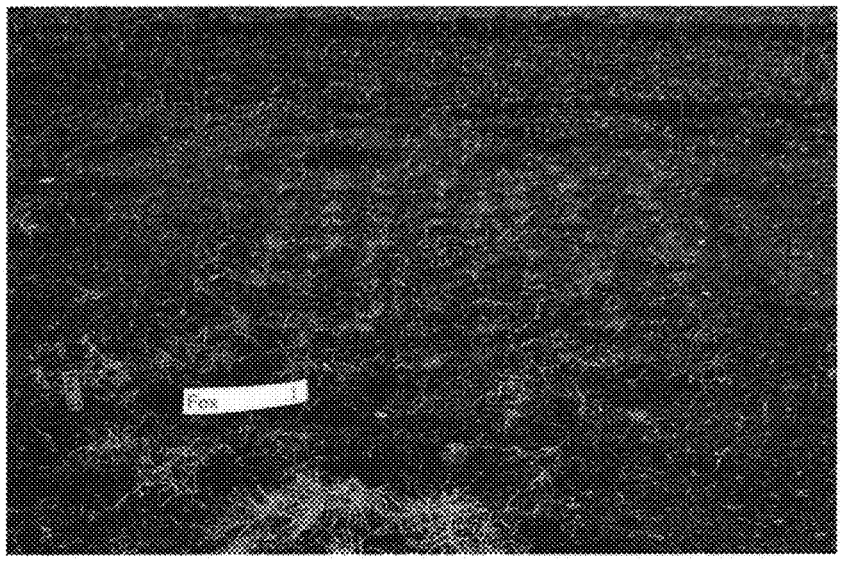
FIG. 4 shows 'Fox' in the close planted plot. Photographing date: Jul. 18, 2013. Photographing site: same as in FIG. 1.
Figure 5:
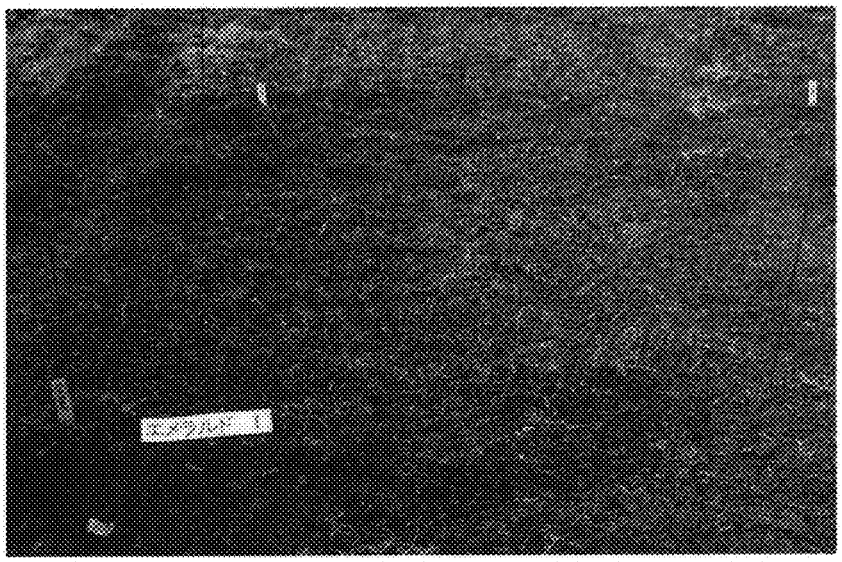
FIG. 5 shows 'Emerald' in the close planted plot. Photographing date: Jul. 18, 2013. Photographing site: same as in FIG. 1.
Figure 6:
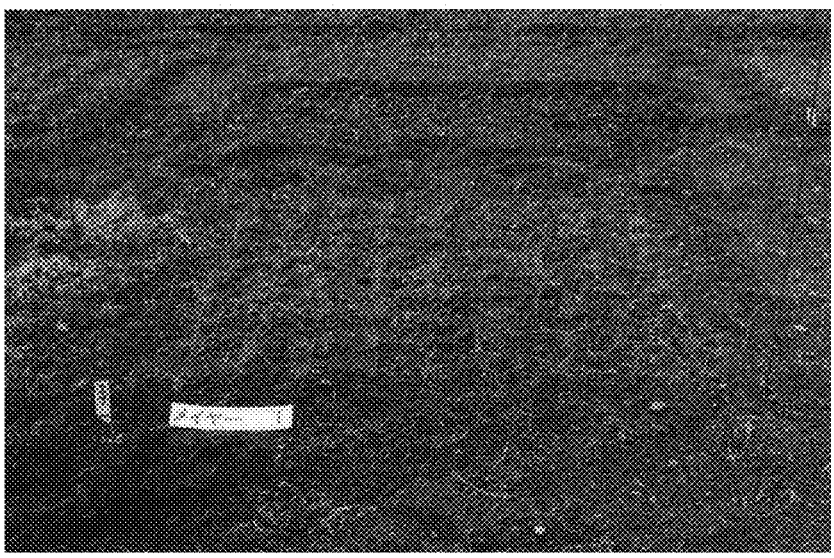
FIG. 6 shows 'Meyer' in the close planted plot. Photographing date: Jul. 18, 2013. Photographing site: same as in FIG. 1.
Figure 7:
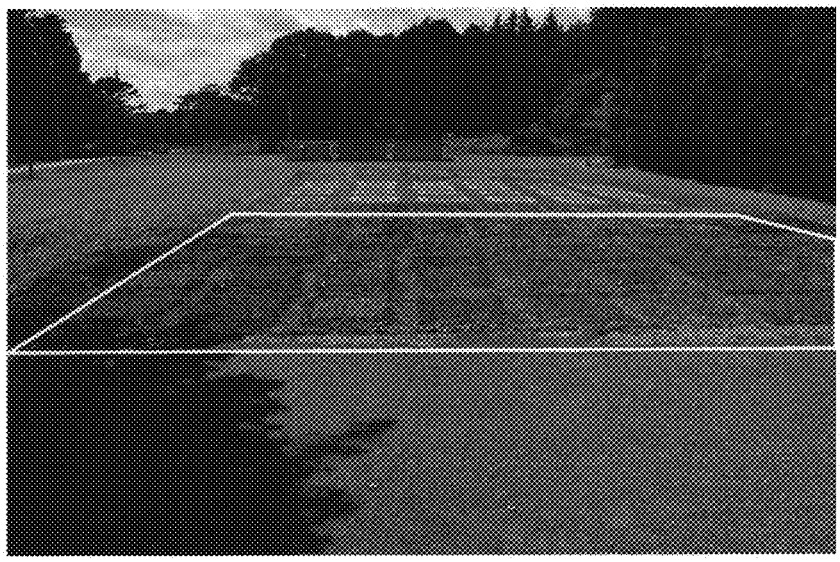
FIG. 7 shows a panoramic view of the test field (in the white frame border), including the test plot of 'Fox'. Photographing date: Sep. 9, 2013. Photographing site: same as in FIG. 1.
Figure 8:
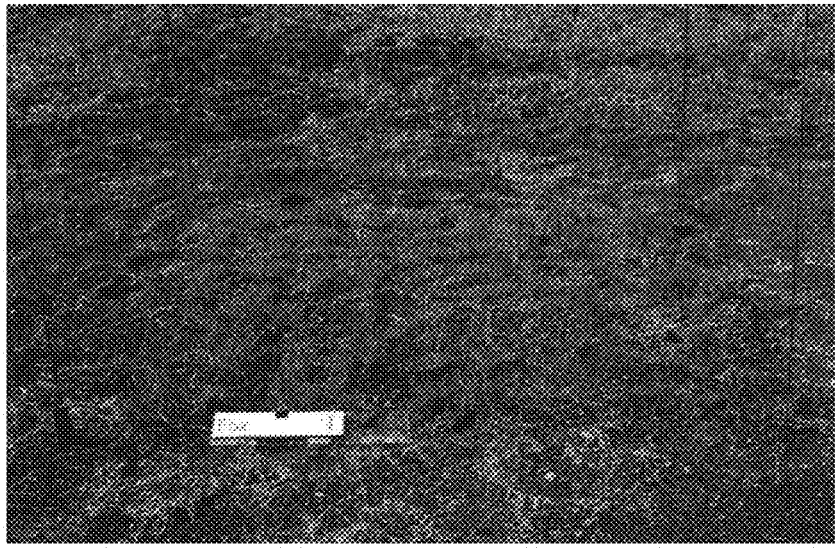
FIG. 8 shows 'Fox' in the close planted plot. Photographing date: Sep. 9, 2013. Photographing site: same as in FIG. 1.
Figure 9:
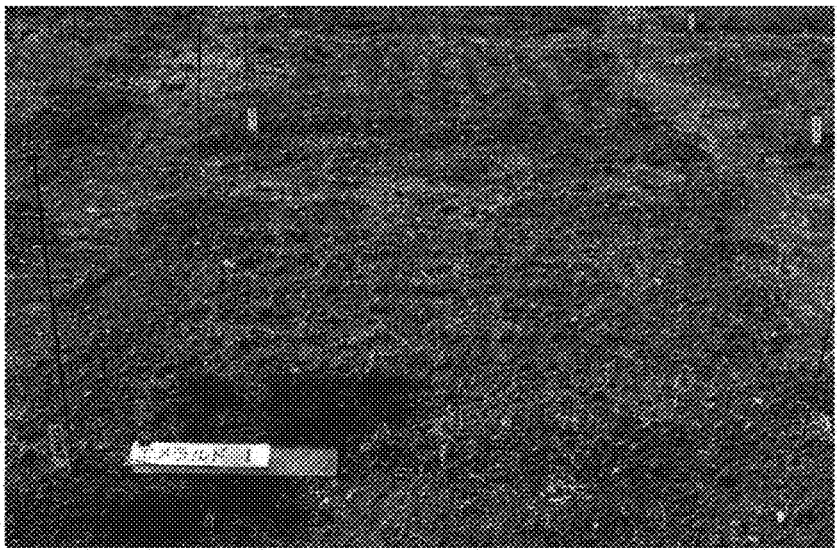
FIG. 9 shows 'Emerald' in the close planted plot. Photographing date: Sep. 9, 2013. Photographing site: same as in FIG. 1.
Figure 10:
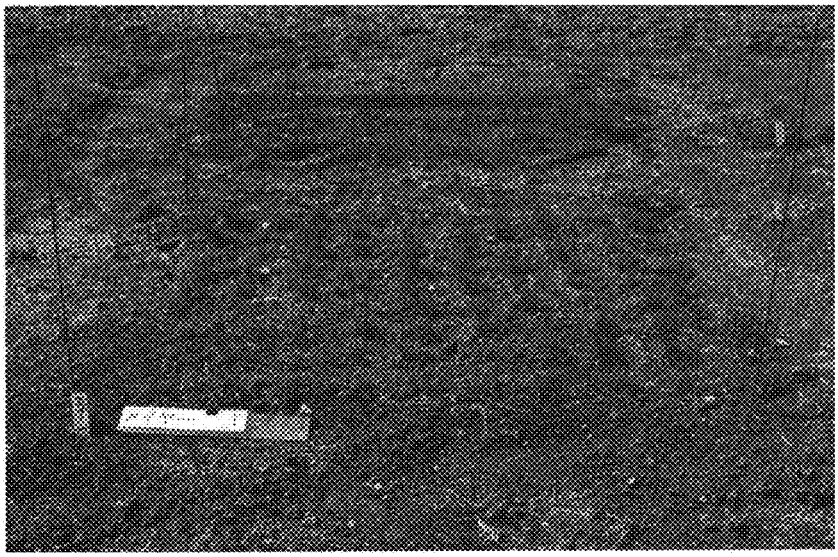
FIG. 10 shows 'Meyer' in the close planted plot. Photographing date: Sep. 9, 2013. Photographing site: same as in FIG. 1.
Figure 11:
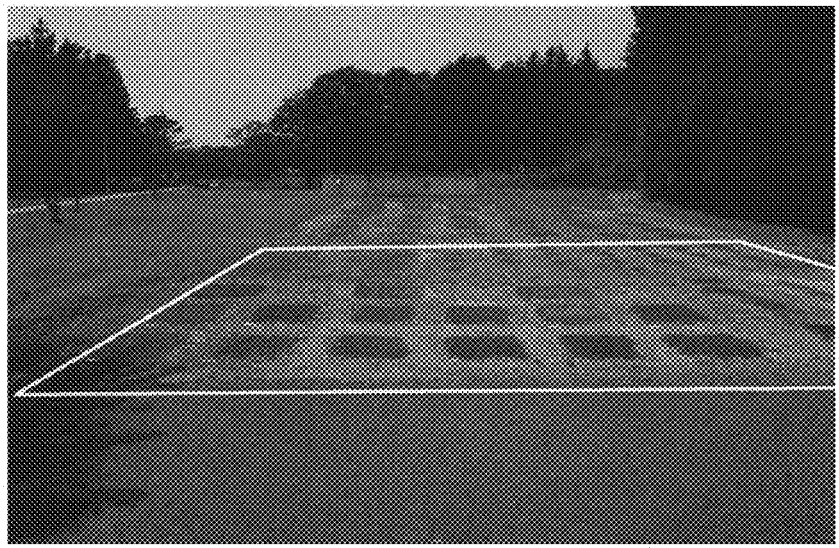
FIG. 11 shows a panoramic view of the test field (in the white frame border), including the test plot of 'Fox'. Photographing date: Jul. 30, 2014. Photographing site: same as FIG. 1.
Figure 12:
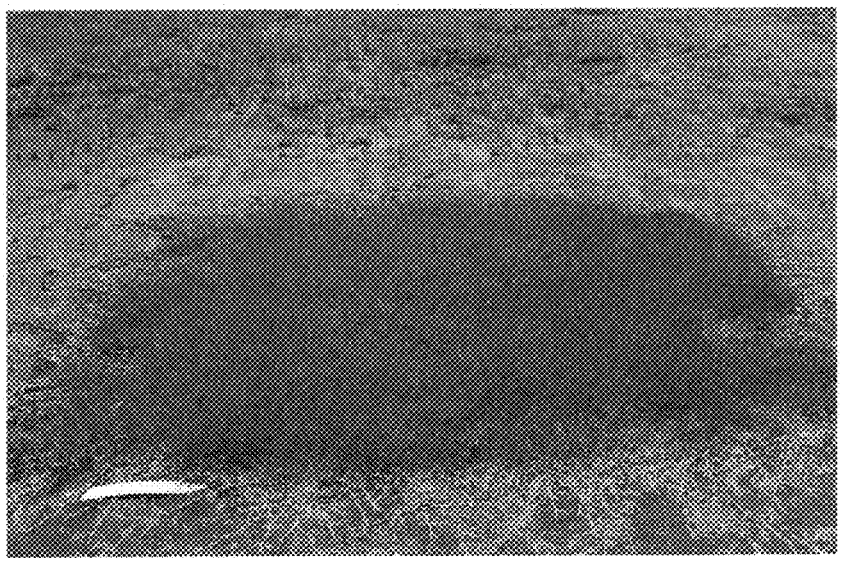
FIG. 12 shows 'Fox' in the close planted plot. Photographing date: Jul. 30, 2014. Photographing site: same as in FIG. 1.
Figure 13:
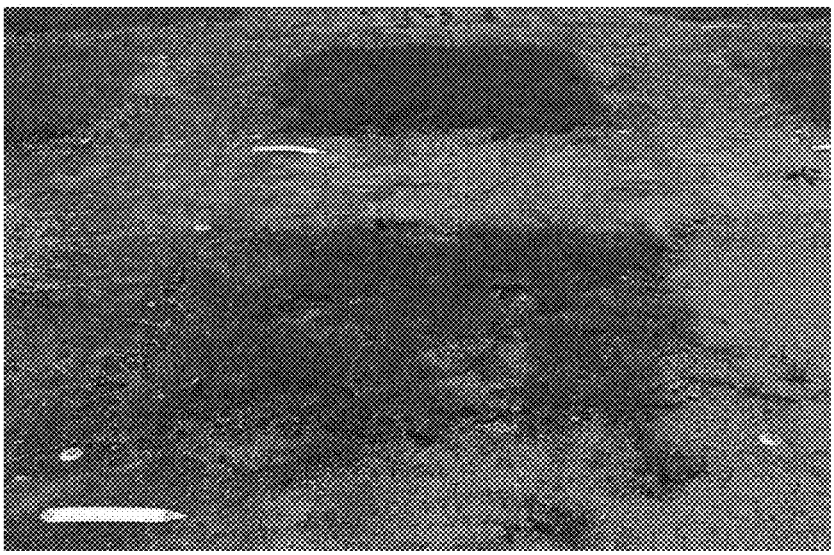
FIG. 13 shows 'Emerald" in the close planted plot. Photographing date: Jul. 30, 2014. Photographing site: same as in FIG. 1.
Figure 14:
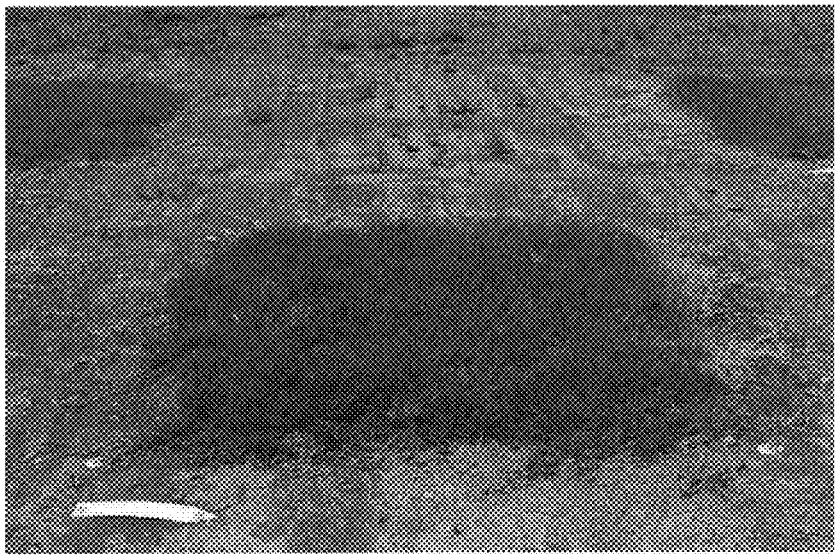
FIG. 14 shows 'Meyer' in the close planted plot. Photographing date: Jul. 30, 2014. Photographing site: same as in FIG. 1.
Figure 15:
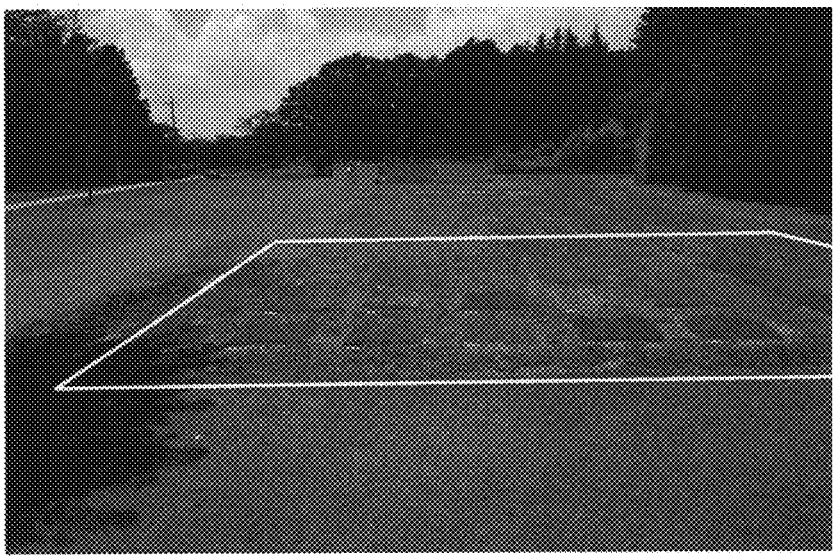
FIG. 15 shows a panoramic view of the test field (in the white frame border), including the test plot of 'Fox'. Photographing date: Jul. 21, 2015. Photographing site: same as in FIG. 1.
Figure 16:
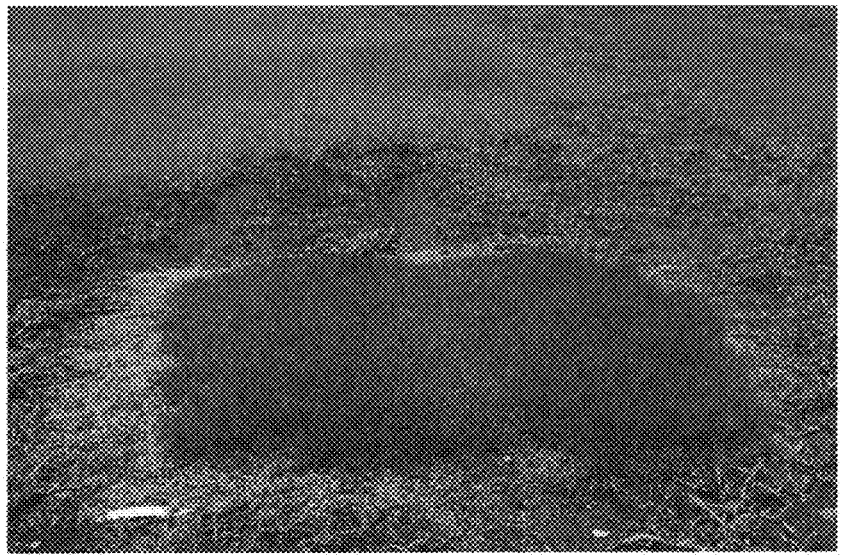
FIG. 16 shows 'Fox' in the close planted plot. Photographing date: Jul. 21, 2015. Photographing site: same as in FIG. 1.
Figure 17:
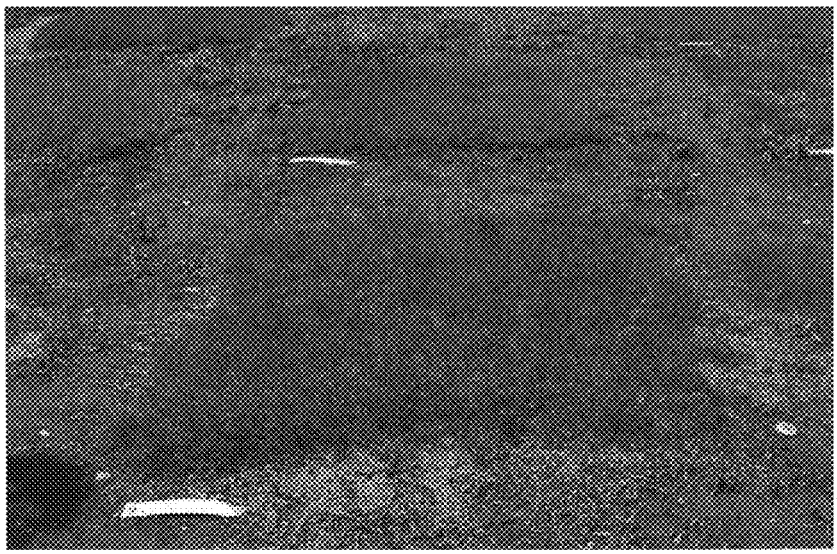
FIG. 17 shows 'Emerald' in the close planted plot. Photographing date: Jul. 21, 2015. Photographing site: same as in FIG. 1.
Figure 18:
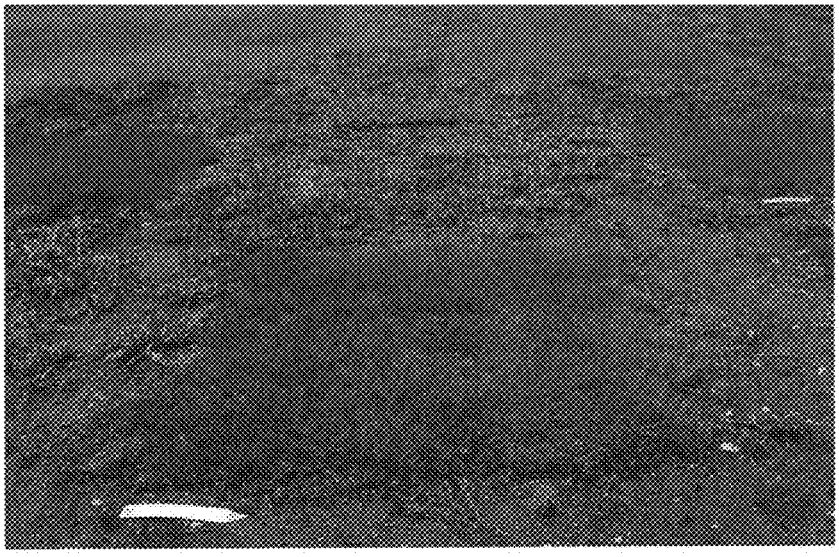
FIG. 18 shows 'Meyer' in the close planted plot. Photographing date: Jul. 21, 2015. Photographing site: same as in FIG. 1.
Figure 19:
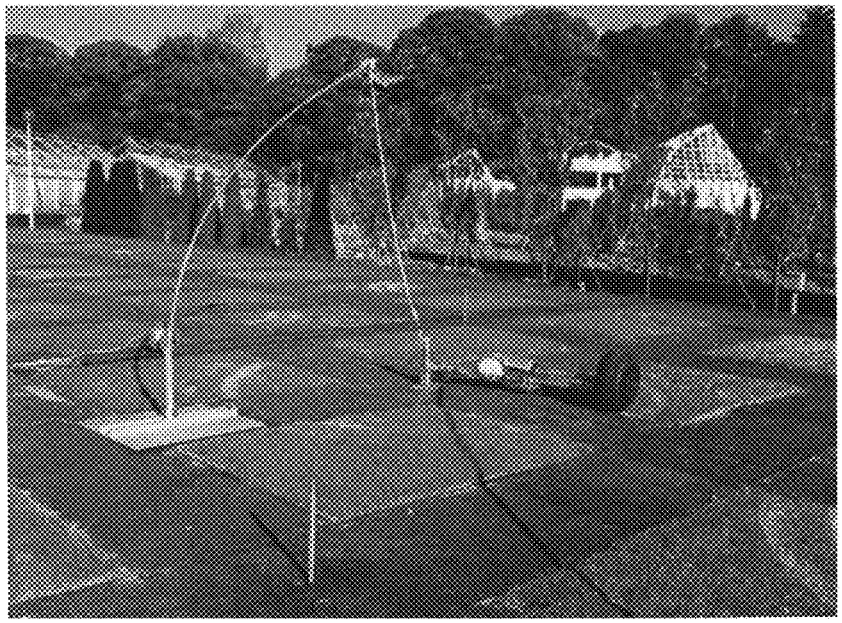
FIG. 19 shows an entire picture of the tread load machine. This picture was taken and provided by Tokyo Metropolitan Agriculture and Forestry Research Center. Photographing date: Nov. 19, 2008. Photographing site: test field in Tokyo Metropolitan Agriculture and Forestry Research Center: Fujimicho, Tachikawa city, Tokyo, Japan.
Figure 20:
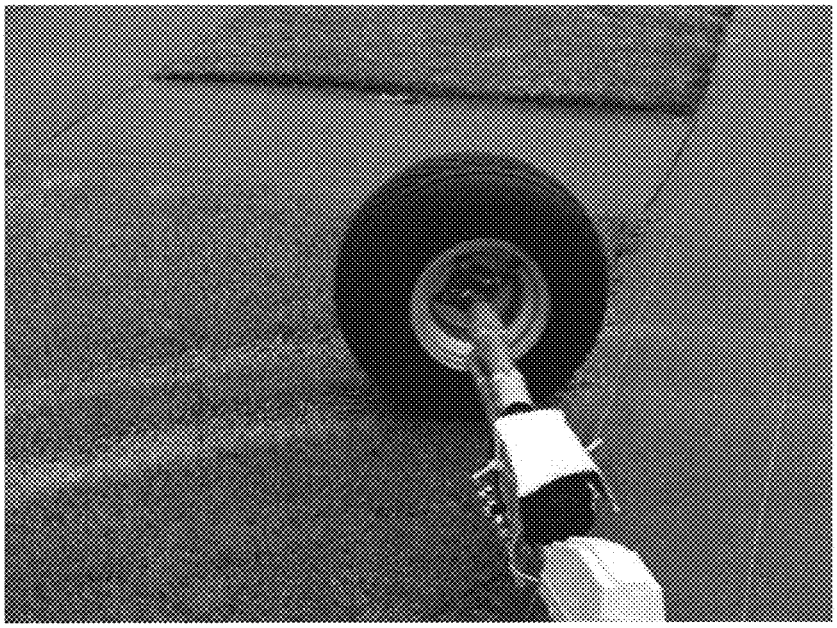
FIG. 20 shows an image of tread pressure damage on turf caused by a tread load machine. This picture was taken and provided by Tokyo Metropolitan Agriculture and Forestry Research Center. Oct. 10, 2008. Photographing site: same as in FIG. 19.

The comparison of stolon thicknesses of 'Fox', 'Emerald' and 'Meyer' (FIG. 2) shows that 'Fox' has thicker stolon than those of 'Emerald' and 'Meyer' (see also Tables 1 and 2). Since 'Fox' has thicker stolon than those of 'Emerald' and 'Meyer', it has higher tolerance to wear than 'Emerald' and 'Meyer'. Furthermore, comparing 'Fox' with 'El Toro' (a variety of *Zoysia japonica*, having relatively high tolerance to tread pressure), 'Fox' has higher tolerance to tread pressure (see Tables 7 and 8 below) and longer green period (see Table 9 below) than 'El Toro'. Therefore, 'Fox' is considered to be promising as *Zoysia* grass for school playground.

In addition, 'Fox' has better summer survival and late fall discoloration than 'Emerald' and 'Meyer' (see Tables 3 and 4 below), and also has higher disease resistance to *Rhizoctonia* patch, rust, and stripe leaf roll than 'Emerald' and 'Meyer' (see Tables 5 and 6 below).

A. REPRODUCTION

After the crossbreeding between the ecotype '286 Togurazaki 6' (seed parent) and the ecotype '226 Nagasaki Akase 6' (pollen parent), and the subsequent selection for properties from the 10 $F_1$ individuals derived from the above-mentioned crossbreeding, 'Fox' was maintained by vegetative propagation. Subsequently, for further tests, several stolons of 'Fox' were collected and grown in 7.5 cm diameter polypots (for tests in individually planted plots) and in 5 cm square peat moss pots (for tests in close planted plots). For the following respective tests, the pot seedlings of 'Fox' were transplanted in 3 replications in test plots.

It is apparent from the Figures provided herein that 'Fox' transplanted in the test plots grew at a more rapid rate than 'Emerald' during the second comparison tests period (July 2013 to July 2015).

B. MORPHOLOGICAL AND GROWTH PROPERTIES

'Fox' was tested for its morphological and growth properties in the period of 2003 to 2006 (the first comparison tests) and in the period of 2013 to 2015 (the second comparison tests), comparing to those of 'Emerald' and 'Meyer'. 'Fox' and 'Emerald' both had no ear emergence in the test cultivations in Nasushiobara city. The stolon thickness of 'Fox' was significantly thicker than those of 'Emerald' and 'Meyer'. The leaf length of 'Fox' was equal to those of 'Emerald' and 'Meyer'. The leaf width of 'Fox' was significantly wider than 'Emerald'. The leaf color of 'Fox' was significantly darker than the leaf color of 'Emerald' (see Tables 1 and 2).

TABLE 1

Morphological Properties (2003 to 2006)

| | Stolon Thickness (mm) | Leaf Length (cm) | Leaf Width (mm) | Leaf Color 1: very pale to 9: very dark | Ear Emergence 1: no emergence 2: spring emergence 3: fall emergence 4: spring and fall emergence |
|---|---|---|---|---|---|
| Fox | 1.94 | 1.99 | 2.74 | 6.5 | 1 |
| Emerald | 1.14 | 2.08 | 1.69 | 5.2 | 1 |
| Meyer | 1.65 | 2.20 | 3.13 | 6.4 | 2 |

The ages of the plants observed for Stolon thickness, Leaf length, Leaf width, and Leaf color were plant age 2, and the ages of the plants observed for Ear emergence were plant ages 1-4.

TABLE 2

Morphological Properties (2013 to 2015)

| | Stolon Thickness (mm) | Leaf Length (cm) | Leaf Width (mm) | Leaf Color 1: very pale to 9: very dark | Ear Emergence 1: no emergence 2: spring emergence 3: fall emergence 4: spring and fall emergence |
|---|---|---|---|---|---|
| Fox | 2.05 | 2.11 | 2.73 | 7.0 | 1 |
| Emerald | 1.27 | 2.02 | 2.02 | 5.0 | 1 |
| Meyer | 1.71 | 2.13 | 3.23 | 7.0 | 2 |

The ages of the plants observed for Stolon thickness, Leaf length, Leaf width, and Leaf color were plant age 2, and the ages of the plants observed for Ear emergence were plant ages 1-3.

The fall discoloration of 'Fox' was significantly later than those of 'Emerald' and 'Meyer' in 2003 fall, and it was equal to that of 'Emerald' and significantly later than that of 'Meyer', in 2004 fall, 2005 fall and 2013 fall. The fall discoloration of 'Fox' in 2014 fall (in the test field of Chubu Green Institute of Chubu Co., Ltd.: Kotoura town, Tottori-prefecture, Japan) was more than one month later than those of 'Emerald' and 'Meyer'. The fall discoloration of 'Fox' in 2015 fall was equal to that of 'Emerald' and 21 days later than that of 'Meyer'. The summer survival of 'Fox' was significantly better than those of 'Emerald' and 'Meyer', and the winter survival of 'Fox' was equal to those of 'Emerald' and 'Meyer' (see Tables 3 and 4).

TABLE 3

Growth Properties (2003 to 2006)

| | Fall Discoloration Date (Month/Day) in 2003 | Fall Discoloration Date (Month/Day) in 2004 | Fall Discoloration Date (Month/Day) in 2005 | Winter Survival 1:very bad to 9:very good | Summer Survival 1:very bad to 9:very good |
|---|---|---|---|---|---|
| Fox | Dec. 6 | Dec. 4 | Nov. 29 | 7.0 | 5.0 |
| Emerald | Dec. 1 | Nov. 28 | Nov. 28 | 7.0 | 3.9 |
| Meyer | Nov. 25 | Nov. 15 | Nov. 23 | 6.3 | 3.1 |

The ages of the plants observed for Fall discoloration date in 2003 were plant age 1, the ages of the plants observed for Fall discoloration date in 2004 were plant age 2, and the ages of the plants observed for Fall discoloration date in 2005 were plant age 3. The ages of the plants observed for Winter survival and Summer survival were plant age 2.

TABLE 4

Growth Properties (2013 to 2015)

| | Fall discoloration date (Month/Day) in 2013 | Fall discoloration date in Kotoura town (Year/Month/Day) | Fall discoloration date in 2015 | Winter survival 1: very bad to 9: very good |
|---|---|---|---|---|
| Fox | Dec. 4 | 2015 Jan. 13 | Dec. 28 | 5.3 |
| Emerald | Dec. 4 | 2014 Dec. 5 | Dec. 28 | 4.3 |
| Meyer | Nov. 29 | 2014 Dec. 5 | Dec. 7 | 5.3 |

The ages of the plants observed for Fall discoloration date in 2013 were plant age 1, the ages of the plants observed for Fall discoloration date in Kotoura town were plant age 2, and the ages of the plants observed for Fall discoloration date in 2015 were plant age 3. The ages of the plants observed for Winter survival were plant age 2.

C. DISEASE RESISTANCE

Furthermore, 'Fox' was also tested for its disease resistance in the period of 2003 to 2006 (the first comparison tests) and in the period of 2013 to 2015 (the second comparison tests), comparing to those of 'Emerald' and 'Meyer'.

In the first comparison tests (2003 to 2006), the disease resistance of 'Fox' to *Rhizoctonia* patch was significantly higher than those of 'Emerald' and 'Meyer', and the disease resistance of 'Fox' to rust was equal to that of 'Emerald' and significantly higher than that of 'Meyer', and finally, the disease resistance of 'Fox' to stripe leaf roll was equal to that of 'Emerald' and significantly higher than that of 'Meyer'.

In the second comparison tests (2013 to 2015), the disease resistance of 'Fox' to *Rhizoctonia* patch was equal to that of 'Emerald' and significantly higher than that of 'Meyer', and the disease resistance of 'Fox' to stripe leaf roll was equal to that of 'Emerald' and significantly higher than that of 'Meyer' (see Tables 5 and 6).

TABLE 5

Disease Resistance (2003 to 2006)

| | Resistance to Rhizoctonia Patch 1: very low to 9: very high | Resistance to Rust 1: very low to 9: very high | Resistance to Stripe Leaf Roll 1: very low to 9: very high |
|---|---|---|---|
| Fox | 7.7 | 8.7 | 9.0 |
| Emerald | 4.3 | 9.0 | 9.0 |
| Meyer | 4.3 | 7.0 | 5.7 |

Scored from the degree of natural pathogenesis. Scores 1 and 9 are defined to be lethal pathogenesis and no pathogenesis, respectively. Scores 2 to 8 are allocated between 1 and 9. The ages of the plants observed for Resistance to *Rhizoctonia* patch were plant age 2, and the ages of the plants observed for Resistance to rust and Resistance to stripe leaf roll were plant age 1.

TABLE 6

Disease Resistance (2013 to 2015)

| | Resistance to Rhizoctonia Patch 1: very low to 9: very high | Resistance to Stripe Leaf Roll 1: very low to 9: very high |
|---|---|---|
| Fox | 6.7 | 9.0 |
| Emerald | 5.3 | 9.0 |
| Meyer | 4.0 | 5.7 |

Scored from the degree of natural pathogenesis. Scores 1 and 9 are defined to be lethal pathogenesis and no pathogenesis, respectively. Scores 2 to 8 are allocated between 1 and 9. The ages of the plants observed for Resistance to *Rhizoctonia* patch and Resistance to stripe leaf roll were plant age 3.

D. TORELANCE TO TREAD PRESSURE

The tolerance to tread pressure of 'Fox' was tested in the test field in Tokyo Metropolitan Agriculture And Forestry Research Center in October 2013 and May 2014, by comparing to 'El Toro', which is a variety of *Zoysia japonica*, having relatively high tolerance to tread pressure. 'Fox' and 'El Toro' were transplanted in the planting bases (composed of 90% washed sand, 5% zeolite and 5% perlite), which were 3 $m^2$ per plot. The tests were carried out in 3 replications. The tread pressure treatments were carried out by giving the tread pressure loads calculated from the research of the action of elementary school children (that is, 100% load (348 person·second/$m^2$) and 50% load (174 person·second/$m^2$) both at 29.3 kg weight (corresponding to the average weight of elementary school children), and no treatment) onto 'Fox' and 'El Toro', using the tread load machine which was developed by Tokyo Metropolitan Agriculture And Forestry Research Center (Japanese Utility Model No. 3155709). The growth states of 'Fox' and 'El Toro' after the tread pressure treatment were evaluated by determining the number of shoots, the sum of stolon lengths, the dry weight of stolons of both varieties.

In both 2013 test and 2014 test, the number of shoots of 'Fox' per square meter was higher than that of 'El Toro', the sum of stolon lengths of 'Fox' per square meter was longer than that of 'El Toro', and the dry weight of stolons of 'Fox' was higher than that of 'El Toro', in all tread pressure treatments (i.e., 100% load, 50% load, and no treatment) (see Tables 7 and 8 below).

TABLE 7

Growth Rate State After Tread Pressure Treatment in October 2013

| | Number of Shoots (number/$m^2$) | | | Stolon Length ($m/m^2$) | | | Dry Weight of Stolon (g) | | |
|---|---|---|---|---|---|---|---|---|---|
| Variety | No treat-ment | 50% | 100% | No treat-ment | 50% | 100% | No treat-ment | 50% | 100% |
| Fox | 11691 | 11040 | 7077 | 293 | 287 | 246 | 134 | 130 | 121 |
| El Toro | 5407 | 3057 | 3680 | 185 | 136 | 156 | 76 | 54 | 78 |

The ages of the plants observed for Number of shoots, Stolon length and Dry weight of stolon were plant age 1.

TABLE 8

Growth Rate State After Tread pressure Treatment in May 2014

| | Number of Shoots (number/$m^2$) | | | Stolon Length ($m/m^2$) | | | Dry Weight of Stolon (g) | | |
|---|---|---|---|---|---|---|---|---|---|
| Variety | No treat-ment | 50% | 100% | No treat-ment | 50% | 100% | No treat-ment | 50% | 100% |
| Fox | 13580 | 13580 | 10701 | 488 | 373 | 352 | 154 | 118 | 136 |
| El Toro | 11796 | 9936 | 10268 | 238 | 251 | 219 | 83 | 55 | 75 |

The ages of the plants observed for Number of shoots, Stolon length and Dry weight of stolon were plant age 2.

In addition, the greening period of 'Fox' determined by observation was about one month longer than that of 'El Toro' (see Table 9 below).

TABLE 9

Greening Period Determined by Observation

| Variety | Greening time | Discoloration time |
|---|---|---|
| Fox | Middle April | Late November |
| El Toro | Late April | Late October |

The ages of the plants observed for Greening time and Discoloration time were plant age 1-2.

As a result, it was discovered that 'Fox' had higher tolerance to tread pressure than 'El Toro', since 'Fox' was less affected by the tread pressure treatment than 'El Toro, the dry weight of stolons of 'Fox' after the tread pressure treatment was larger than that of 'El Toro, and the growth revival of 'Fox' after the tread pressure treatment occurred more readily than in 'El Toro', and further, 'Fox' had a longer green period (middle April to late November) than 'El Toro'. Therefore, 'Fox' is considered to be promising as *Zoysia* grass suitable for school playgrounds.

E. TEST FOR UNIFORMITY AND DISTINCTNESS OF 'Fox' USING SSR MARKERS

In order to confirm the uniformity and distinctness of 'Fox' clonal line at the DNA level, the tests for uniformity and distinctness were carried out by using the SSR markers (Tsuruta S., et al., Development and characterization of simple sequence repeat markers in *Zoysia japonica*, Steud. Grassland Science 51: 249-257 (2005)), which were developed by the National Institute of Livestock and Grassland Science (Tochigi-prefecture, Japan).

1. Materials and Methods

With regard to 'Fox', 12 leaf samples were collected from the clone storage field, and 2 leaf samples were collected from the planters in the greenhouse, and subsequently, the DNAs were extracted from these 14 leaf samples. For each sample, a plurality of leaves (which were able to be confirmed as being derived from one clone) were collected. The DNAs extracted from 'Emerald' and 'Meyer', as control varieties, were also tested. The SSR markers used, and the experimental conditions are shown as follows (see Tables 10 to 13 below).

TABLE 10

6 Types of SSR Markers Used for Tests (all derived from the genomic DNA of *Zoysia japonica* 'Asagake')

| Marker Name | Motif | Primer Sequence (5'-3') Forward | SEQ ID NO: |
|---|---|---|---|
| ZjAG115 | $(AG)^{13}$ | GAACAAGAGTA GTGGCGTCA | 1 |
| ZjAG120 | $(AG)^{8}$ | GCGGCTACTCTA CTCCACTACAG | 3 |
| ZjAG125 | $(AG)^{17}$ | TAACTACTAGCC GATCAAGA | 5 |
| ZjAG133 | $(AG)^{6}AA(AG)^{28}$ | TGGGCTTAGTGC TACGAATGTG | 7 |
| ZjAG140 | $(TG)^{10}(AG)^{10}$ | CTTACACCCCAC ATCAACTG | 9 |
| ZjAG143 | $(AG)^{13}AA(GA)^{4}$ | CGCAACTTCAAA TCCTAC | 11 |

| Marker Name | Primer Sequence (5'-3') Reverse | SEQ ID NO: | Amplified Chain Length (bp) |
|---|---|---|---|
| ZjAG115 | GCACGCATCGTT TTGGTTCAAT | 2 | 155 |
| ZjAG120 | TGTAGGTGAGGG ACGGATAAAG | 4 | 117 |
| ZjAG125 | TACTTGTTCATTG CCATTATCC | 6 | 179 |
| ZjAG133 | AACCTGCCTATCT GTGCGTATG | 8 | 136 |
| ZjAG140 | ACAGACATAGGG CTCATTAGTG | 10 | 146 |
| ZjAG143 | AGAACTAAGCAA AATTGGTCCC | 12 | 129 |

Amplified chain length indicates the chain length of the amplified fragment based on the base sequence.

TABLE 11

Reaction Composition for PCR Amplification

| Composition | Used amount |
|---|---|
| 5 × primeSTAR Buffer (TaKaRa) | 2.0 μl |
| dNTP Mixture (2.5 mM each) | 0.8 μl |
| Forward Primer (5 pmol/μl) | 1.0 μl |
| Reverse Primer (5 pmol/μl) | 1.0 μl |
| PrimeSTAR HS Taq (TaKaRa) | 0.1 μl |
| SDW | 4.1 μl |
| Template DNA (25 ng/μl) | 1.0 μl |
| Total | 10.0 μl |

TABLE 12

Reaction Conditions for PCR Amplification

| Temperatures | Times | Cycle |
|---|---|---|
| 98° C. | 3 minutes | 1 cycle |
| 98° C. | 20 seconds | 30 cycles |
| 56° C. | 20 seconds | |
| 72° C. | 30 seconds | |
| 4° C. | ∞ | 1 cycle |

TABLE 13

Electrophoresis Condition Using the Sequencer ABI3130x1

| Composition | Used amount |
|---|---|
| Formamide | 13.75 μl |
| ROX500 | 0.25 μl |
| PCR Product (150-fold diluted with sterile water) | 1.00 μl |
| Total | 15.00 μl |

2. Results

Since there was no difference in the size of amplified DNA region among the 14 samples of 'Fox', these samples were identified as having the same genotype. In contrast, there was difference in the size of amplified DNA region among 'Fox', 'Emerald' and 'Meyer', and thus it was determined that 'Fox' has a genotype different from 'Emerald' and 'Meyer' (see Table 14 below).

TABLE 14

Typing Results Based On the Electrophoresis Data Obtained by the Sequencer ABI3130x1

| Sample | Marker ZjAG115 | ZjAG120 | ZjAG125 |
|---|---|---|---|
| Fox (planter 01) | 146/155/228/236 | 111/117 | 186/188 |
| Fox (planter 02) | 146/155/228/236 | 111/117 | 186/188 |
| Fox (field 01) | 146/155/228/236 | 111/117 | 186/188 |
| Fox (field 02) | 146/155/228/236 | 111/117 | 186/188 |
| Fox (field 03) | 146/155/228/236 | 111/117 | 186/188 |
| Fox (field 04) | 146/155/228/236 | 111/117 | 186/188 |
| Fox (field 05) | 146/155/228/236 | 111/117 | 186/188 |
| Fox (field 06) | 146/155/228/236 | 111/117 | 186/188 |
| Fox (field 07) | 146/155/228/236 | 111/117 | 186/188 |
| Fox (field 08) | 146/155/228/236 | 111/117 | 186/188 |
| Fox (field 09) | 146/155/228/236 | 111/117 | 186/188 |
| Fox (field 10) | 146/155/228/236 | 111/117 | 186/188 |
| Fox (field 11) | 146/155/228/236 | 111/117 | 186/188 |
| Fox (field 12) | 146/155/228/236 | 111/117 | 186/188 |
| Emerald | 144/236 | 121 | 177/186 |
| Meyer | 144/236 | 104/123 | 174/186 |

| Sample | Marker ZjAG133 | ZjAG140 | ZjAG143 |
|---|---|---|---|
| Fox (planter 01) | 88/95 | 131/146 | 114/124 |
| Fox (planter 02) | 88/95 | 131/146 | 114/124 |
| Fox (field 01) | 88/95 | 131/146 | 114/124 |
| Fox (field 02) | 88/95 | 131/146 | 114/124 |

TABLE 14-continued

| Typing Results Based On the Electrophoresis Data Obtained by the Sequencer ABI3130x1 | | | |
|---|---|---|---|
| Fox (field 03) | 88/95 | 131/146 | 114/124 |
| Fox (field 04) | 88/95 | 131/146 | 114/124 |
| Fox (field 05) | 88/95 | 131/146 | 114/124 |
| Fox (field 06) | 88/95 | 131/146 | 114/124 |
| Fox (field 07) | 88/95 | 131/146 | 114/124 |
| Fox (field 08) | 88/95 | 131/146 | 114/124 |
| Fox (field 09) | 88/95 | 131/146 | 114/124 |
| Fox (field 10) | 88/95 | 131/146 | — |
| Fox (field 11) | — | 131/146 | 114/124 |
| Fox (field 12) | — | 131/146 | 114/124 |
| Emerald | 93/130 | 131/146 | 110/126 |
| Meyer | 86/93 | 135 | 108/124 |

Numbers indicate the sizes of each allele (bp).
" " indicates missing values.

The above results confirm the uniformity of the 'Fox' clone and the distinctness of 'Fox' from the other major varieties of *Zoysia*.

G. DIFFERENCE IN MORPHOLOGICAL AND GROWTH PROPERTIES FROM PARENTS

The stolon thickness of 'Fox' was considerably wider than that of the ecotype '286 Togurazaki 6' (seed parent), and with respect to ear emergence, 'Fox' had no ear emergence in 2003-2006 and 2013-2016, but the ecotype '226 Nagasaki Akase 6' (pollen parent) had relatively abundant ear emergence (see Table 15). The greening period of 'Fox' was middle April to late November (see Table 9 and Table 16), but that of the ecotype '226 Nagasaki Akase 6' (pollen parent) was late April to late October (see Table 16). Therefore, the greening period of 'Fox' was one month longer than the ecotype '226 Nagasaki Akase 6' (pollen parent).

TABLE 15

Comparison of Morphological Properties between 'Fox' and the parents varieties (the ecotype '286 Togurazaki 6' (seed parent) and the ecotype '226 Nagasaki Akase 6' (pollen parent)). The research of the parents varieties was conducted in 1992 to 1999.

| Cultivar | Stolon thickness (mm) | Leaf length (cm) 1: extremely short to 9: extremely long | Leaf width (mm) 1: extremely slender to 9: extremely wide |
|---|---|---|---|
| Fox (2003-2006) | 1.94 | 1.99 (3) | 2.74 (5) |
| Fox (2013-2016) | 2.05 | 2.11 (3) | 2.73 (5) |

| Cultivar | Leaf color (1: very pale to 9: very dark) | Ear emergence 1: no 2: spring 3: fall 4: spring and fall |
|---|---|---|
| Fox (2003-2006) | 6.5 | 1 |
| Fox (2013-2016) | 7.0 | 1 |

TABLE 15-continued

Comparison of Morphological Properties between 'Fox' and the parents varieties (the ecotype '286 Togurazaki 6' (seed parent) and the ecotype '226 Nagasaki Akase 6' (pollen parent)). The research of the parents varieties was conducted in 1992 to 1999.

| Ecotypes | Stolon thickness (mm) | Leaf length 1: extremely short to 9: extremely long | Leaf width 1: extremely slender to 9: extremely wide |
|---|---|---|---|
| 286 Togurazaki 6 | 0.9 | 2 | 1 |
| 226 Nagasaki Akase 6 | 1.6 | 5 | 5 |

| Ecotypes | Leaf color 1: extremely light to 9: extremely dark | Heading 1: extremely little to 9: extremely abundant |
|---|---|---|
| 286 Togurazaki 6 | — | 3 |
| 226 Nagasaki Akase 6 | 5 | 7 |

The numerals 3 and 5 in the brackets after Leaf length (cm) and Leaf width (mm) of 'Fox' indicate the scores for Leaf length and Leaf width. Score 3 indicates "short", and Score 5 indicates "middle".

TABLE 16

Comparison of Spring greening date and Fall discoloration date, and Summer survival between 'Fox' and the parents varieties (the research of the parents varieties was conducted in 1992 to 1999)

| Cultivar | Spring greening date in Nasushiobara (Month/Day) | Fall discoloration date in Nasushiobara (Month/Day) | Summer survival (1: very bad to 9: very good) |
|---|---|---|---|
| Fox (2003-2006) | Apr. 19-4/30 | Nov. 29-Dec. 6 | 5.0 |
| Fox (2013-2016) | Apr. 14 | Dec. 4-Dec. 28 | — |

| Ecotypes | Greening time (Year/Month/Day) | Coloring time (Year/Month/Day) | Summer survival 1: extremely poor to 9: extremely excellent |
|---|---|---|---|
| 286 Togurazaki 6 | 1992 Apr. 5 | — | 7 |
| 226 Nagasaki Akase 6 | 1992 Apr. 26 | 1993 Oct. 22 | 7 |

TABLE 17

Comparison of Resistance to rust between 'Fox' and the parents variety (the research of the parents variety was conducted in 1992 to 1999)

| Cultivar | Resistance to rust 1: very low to 9: very high |
|---|---|
| Fox (2003-2006) | 8.7 |
| Fox (2013-2016) | — |

| Ecotypes | Crown rust resistance in 1992 1: Extremely low to 9: Extremely high | Crown rust resistance in 1999 1: Extremely low to 9: Extremely high |
|---|---|---|
| 286 Togurazaki 6 | 7 | 1 |
| 226 Nagasaki Akase 6 | 9 | 1 |

SEQUENCE LISTING

<160> NUMBER OF SEQ ID NOS: 12

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1 gaacaagagt agtggcgtca 20

<210> SEQ ID NO 2
<211> LENGTH: 22
<212> TYPE: DNA
<213> ORGANISM: Artificial
<220> FEATURE:
<223> OTHER INFORMATION: primer

<400> SEQUENCE: 2 gcacgcatcg ttttggttca at 22

<210> SEQ ID NO 3
<211> LENGTH: 23
<212> TYPE: DNA
<213> ORGANISM: Artificial
<220> FEATURE:
<223> OTHER INFORMATION: primer

<400> SEQUENCE: 3 gcggctactc tactccacta cag 23

<210> SEQ ID NO 4
<211> LENGTH: 22
<212> TYPE: DNA
<213> ORGANISM: Artificial
<220> FEATURE:
<223> OTHER INFORMATION: primer

<400> SEQUENCE: 4 tgtaggtgag ggacggataa ag 22

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5 taactactag ccgatcaaga 20

<210> SEQ ID NO 6
<211> LENGTH: 22
<212> TYPE: DNA
<213> ORGANISM: Artificial
<220> FEATURE:
<223> OTHER INFORMATION: primer

<400> SEQUENCE: 6 tacttgttca ttgccattat cc 22

<210> SEQ ID NO 7
<211> LENGTH: 22

-continued

```
<212> TYPE: DNA
<213> ORGANISM: Artificial
<220> FEATURE:
<223> OTHER INFORMATION: primer

<400> SEQUENCE: 7

tgggcttagt gctacgaatg tg                                              22


<210> SEQ ID NO 8
<211> LENGTH: 22
<212> TYPE: DNA
<213> ORGANISM: Artificial
<220> FEATURE:
<223> OTHER INFORMATION: primer

<400> SEQUENCE: 8

aacctgccta tctgtgcgta tg                                              22


<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9

cttacacccc acatcaactg                                                 20


<210> SEQ ID NO 10
<211> LENGTH: 22
<212> TYPE: DNA
<213> ORGANISM: Artificial
<220> FEATURE:
<223> OTHER INFORMATION: primer

<400> SEQUENCE: 10

acagacatag ggctcattag tg                                              22


<210> SEQ ID NO 11
<211> LENGTH: 18
<212> TYPE: DNA
<213> ORGANISM: Artificial
<220> FEATURE:
<223> OTHER INFORMATION: primer

<400> SEQUENCE: 11

cgcaacttca aatcctac                                                   18


<210> SEQ ID NO 12
<211> LENGTH: 22
<212> TYPE: DNA
<213> ORGANISM: Artificial
<220> FEATURE:
<223> OTHER INFORMATION: primer

<400> SEQUENCE: 12

agaactaagc aaaattggtc cc                                              22
```

What is claimed is:

1. A new and distinct variety of *Zoysia matrella* plant named ‘Fox,’ as described and illustrated herein.

* * * * *